(12) United States Patent
Chen et al.

(10) Patent No.: US 10,308,641 B2
(45) Date of Patent: Jun. 4, 2019

(54) CRYSTAL FORM OF 3-(6-(1-(2,2-DIFLUOROBENZO[D][1,3]DIOXO-LE-5-YL)CYCLOPROPANE FORMAMIDO)-3-METHYLPYRIDINE-2-YL)-BENZOIC ACID AND PREPARATION METHOD THEREOF

(71) Applicant: CRYSTAL PHARMATECH CO., LTD., Suzhou, Jiangsu (CN)

(72) Inventors: Minhua Chen, Jiangsu (CN); Yanfeng Zhang, Jiangsu (CN); Kai Liu, Jiangsu (CN); Po Zou, Jiangsu (CN); Xiaoyu Zhang, Jiangsu (CN)

(73) Assignee: Crystal Pharmatech Co., Ltd., Suzhou, Jiangsu (CN)

( * ) Notice: Subject to any disclaimer, the term of this patent is extended or adjusted under 35 U.S.C. 154(b) by 0 days.

(21) Appl. No.: 15/751,205

(22) PCT Filed: Aug. 11, 2016

(86) PCT No.: PCT/CN2016/094589
§ 371 (c)(1),
(2) Date: Feb. 8, 2018

(87) PCT Pub. No.: WO2017/025045
PCT Pub. Date: Feb. 16, 2017

(65) Prior Publication Data
US 2018/0230136 A1    Aug. 16, 2018

(30) Foreign Application Priority Data
Aug. 11, 2015 (CN) .......................... 2015 1 0489485

(51) Int. Cl.
C07D 405/12    (2006.01)
A61K 31/443   (2006.01)
A61K 31/47    (2006.01)
A61P 11/00    (2006.01)

(52) U.S. Cl.
CPC .......... *C07D 405/12* (2013.01); *A61K 31/443* (2013.01); *A61K 31/47* (2013.01); *A61P 11/00* (2018.01); *C07B 2200/13* (2013.01)

(58) Field of Classification Search
CPC .... C07D 405/12; A61K 31/443; A61K 31/47; C07B 2200/13; A61P 11/00
USPC ....................................................... 514/312
See application file for complete search history.

(56) References Cited

U.S. PATENT DOCUMENTS

2013/0186801 A1*  7/2013  Verwijs ............... A61K 9/28
                                                                 206/570

FOREIGN PATENT DOCUMENTS

| JP | 2015504920 A | 2/2015 |
| WO | 2009073757 A1 | 6/2009 |
| WO | 2010037066 A2 | 4/2010 |
| WO | 2010138484 A2 | 12/2010 |
| WO | 2013112804 A1 | 8/2013 |

OTHER PUBLICATIONS

Noriaki Hirayama, Organic Compound Crystal Production Manual: Principle and Know-How, Maruzen Co., Ltd., Japan, Jul. 25, 2008, p. 17-23, 37-40, 45-51, 57-65.
Kazuhide Ashizawa, Crystal Analysis Science of Polymorphism in Pharmaceuticals, Maruzen Co., Ltd., Japan, Sep. 20, 2002, p. 56-102, 304-317.
Noriyuki Takata, API form screening and selection in drug discovery stage, PHARM Stage, vol. 6, No. 10, 2007, 20-25.
Akira Ogata, Operation of Chemical Experiments, Nankodo Co., Ltd., Japan, Nov. 20, 1963, p. 366-399.

* cited by examiner

*Primary Examiner* — Rita J Desai
(74) *Attorney, Agent, or Firm* — VLP Law Group LLP; Kent H. Cheng

(57) ABSTRACT

The present disclosure provides crystalline form A of 3-(6-(1-(2, 2-difluorobenzo [d] [1, 3] dioxo-5-yl) cyclopropanecarboxamido)-3-methylpyridin-2-yl) benzoic acid and process of preparation thereof. The crystalline form A has low hygroscopicity, good stability, is convenient to store. It has higher solubility than that of prior art and therefore plays an important role in further optimization and development of the drug.

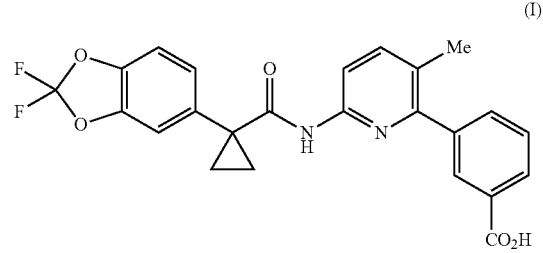

8 Claims, 5 Drawing Sheets

CRYSTAL FORM OF 3-(6-(1-(2,2-DIFLUOROBENZO[D][1,3]DIOXOLE-5-YL)CYCLOPROPANE FORMAMIDO)-3-METHYLPYRIDINE-2-YL) BENZOIC ACID AND PREPARATION METHOD THEREOF

TECHNICAL FIELD

The present disclosure relates to the field of pharmaceutical chemistry, particularly relates to crystalline form of 3-(6-(1-(2,2-difluorobenzo [d] [1,3] dioxol-5-yl) cyclopropanecarboxamido)-3-methylpyridin-2-yl) benzoic acid and process of preparation thereof.

BACKGROUND

Lumacaftor is developed by Vertex and combined with Ivacaftor for the treatment of cystic fibrosis (CF) in patients aged 12 years and older who have the F508del mutation in the cystic fibrosis transmembrane conductance regulator (CFTR). Combination of Lumacaftor/Ivacaftor was approved in the United States on Jul. 2, 2015 under the brand name Orkambi. The chemical name of Lumacaftor is 3-(6-(1-(2,2-difluorobenzo [d] [1,3] dioxol-5-yl) cyclopropanecarboxamido)-3-methylpyridin-2-yl) benzoic acid, and the structure is shown as formula (I):

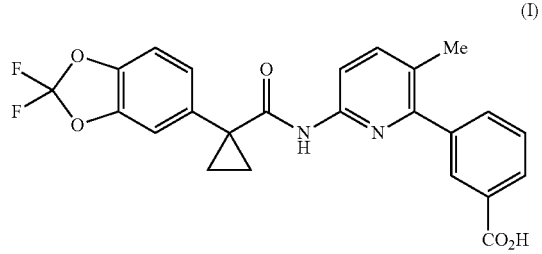 [SMILES: Cc1ccc(NC(=O)C2(c3ccc4c(c3)OC(F)(F)O4)CC2)nc1-c1cccc(C(=O)O)c1]

(I)

CN101910156A disclosed crystalline Form I of Lumacaftor and Form I has an X-ray powder diffraction pattern comprising the following 2theta values measured using CuKα radiation: 15.2-15.6°, 16.1-16.5°, 14.6-15.0°, 17.6-18.0° and 14.3-14.7°. Form I can be obtained by suspending the hydrochloride of compound of formula (I) in water. Additionally, the patent disclosed another method to obtain Form I through intermediate of compound of formula (I). The preparation method of the new crystalline form in present disclosure is directly obtained from compound of formula (I) free form, which is different from that of Form I in CN101910156A.

As is known to the skilled in the art, the presence of new solid polymorphic forms of a known chemical substance is unpredictable. The existence of the polymorphic compound or the number of the polymorphic forms is also unpredictable. In addition, it is also unpredictable under what conditions to obtain a specific form, and how are the characteristics of the polymorphic form. Since the properties (e.g., solubility, stability) of each polymorph of the compound cause the different performance on drug's application and storage, it is necessary to study all solid forms, including all polymorphic forms to provide drugs with improved stability or solubility.

CN101910156A disclosed crystalline Form I but there is no description on the characteristics such as stability and solubility. The inventor of the present disclosure found a new crystalline form of Lumacaftor with better characteristics. The crystalline form in present disclosure has good stability and higher solubility than prior art. It has unexpected technical effect and great value for further development of the drug.

SUMMARY

To solve the problems of prior art, the objectives of present disclosure are to provide a novel crystalline form of compound of formula (I) that has good stability and higher solubility, and the novel crystalline form is designated as crystalline Form A, which can be obtained directly by compound of formula (I) free form.

The crystalline Form A of the present disclosure, wherein the X-ray powder diffraction pattern (CuKα radiation) at 25° C. shows characteristic peaks at 2theta values of 8.8°±0.2°, 21.2°±0.2°, 22.2°±0.2°.

Furthermore, the crystalline Form A of the present disclosure, wherein the X-ray powder diffraction pattern shows one or more characteristic peaks at 2theta values of 9.8°±0.2°, 18.1°±0.2°, 23.5°±0.2°. Preferably, the crystalline Form A of the present disclosure, wherein the X-ray powder diffraction pattern shows characteristic peaks at 2theta values of 9.8°±0.2°, 18.1°±0.2°, 23.5°±0.2°.

Furthermore, the crystalline Form A of the present disclosure, wherein the X-ray powder diffraction pattern shows one or more characteristic peaks at 2theta values of 10.6°±0.2°, 16.2°±0.2°, 20.0°±0.2°; Preferably, the crystalline Form A of the present disclosure, wherein the X-ray powder diffraction pattern shows characteristic peaks at 2theta values of 10.6°±0.2°, 16.2°±0.2°, 20.0°±0.2°.

The crystalline Form A of the present disclosure, wherein the X-ray powder diffraction pattern (CuKα radiation) at 25° C. shows one or more characteristic peaks at 2theta values of 8.8°±0.2°, 21.2°±0.2°, 22.2°±0.2°, 10.6°±0.2°, 18.1°±0.2°, 23.5°±0.2°, 9.8°±0.2°, 16.2°±0.2°, 20.0°±0.2°.

In a specific and preferred embodiment, the X-ray powder diffraction pattern of Form A is substantially as depicted in FIG. 1. Furthermore, the X-ray powder diffraction pattern shows 28 diffraction peaks and the position and intensity of peaks are listed in table 1.

In another specific and preferred embodiment, the X-ray powder diffraction pattern of Form A shows 23 diffraction peaks and the position and intensity of peaks are listed in table 2.

In a specific and preferred embodiment, the X-ray powder diffraction pattern of Form A shows 26 diffraction peaks and the position and intensity of peaks are listed in table 3.

Preferably, the crystalline Form A of the present disclosure, wherein the differential scanning calorimetry (DSC) thermogram shows an endothermic peaks when heated to around 195° C. (onset temperature), and the DSC thermogram is substantially as depicted in FIG. 2. The melting point (initial melting) of Form A is 193V~197° C.

The IR spectrum of crystalline Form A of present disclosure is shown in FIG. 4, comprising one or more peaks at 428.02 $cm^{-1}$, 440.02 $cm^{-1}$, 552.63 $cm^{-1}$, 633.98 $cm^{-1}$, 653.98 $cm^{-1}$, 672.13 $cm^{-1}$, 703.67 $cm^{-1}$, 719.88 $cm^{-1}$, 747.06 $cm^{-1}$, 758.22 $cm^{-1}$, 773.98 $cm^{-1}$, 819.54 $cm^{-1}$, 827.73 $cm^{-1}$, 863.16 $cm^{-1}$, 907.65 $cm^{-1}$, 941.69 $cm^{-1}$, 964.44 $cm^{-1}$, 999.06 $cm^{-1}$, 1034.29 $cm^{-1}$, 1070.98 $cm^{-1}$, 1083.97 $cm^{-1}$, 1111.81 $cm^{-1}$, 1165.13 $cm^{-1}$, 1235.34 $cm^{-1}$, 1303.65 $cm^{-1}$, 1374.39 $cm^{-1}$, 1409.47 $cm^{-1}$, 1421.75 $cm^{-1}$, 1446.91 $cm^{-1}$, 1468.87 $cm^{-1}$, 1505.25 $cm^{-1}$, 1589.40 $cm^{-1}$, 1607.45 $cm^{-1}$, 1673.39 $cm^{-1}$, 1693.20 $cm^{-1}$, 1920.00 $cm^{-1}$, 2546.90 $cm^{-1}$, 2657.45 $cm^{-1}$, 3011.44 $cm^{-1}$ (±2 $cm^{-1}$).

Another objective of the present disclosure is to provide a process of preparing crystalline Form A of compound of formula (I). The method comprises dissolving compound of formula (I) in ketones or the mixture of ketones and ethers, and white solid is obtained by evaporation at the temperature of 20-80° C.

Preferably, said temperature is 30° C.-70° C., more preferably, said temperature is 40° C.-60° C.

Preferably, volume ratio of mixture of ketones and ethers is 1:1 to 1:4.

According to the present disclosure, preferably, said ketones are acetone or methyl isobutyl ketone (MIBK), said ether is methyl tertiary butyl ether (MTBE).

According to a specific and preferred embodiment, Form A is obtained by dissolving the compound of formula (I) into MIBK or the mixture of acetone and MTBE. Form A is obtained after evaporation at 50° C. Preferably, the volume ratio of mixture of acetone or MIBK with MTBE is 1:1 to 1:4.

Furthermore, the content of compound of formula (I) in said solvent (mg/mL) is 1-20; preferably, the content of compound of formula (I) in said solvent is 5-15; more preferably, the content of compound of formula (I) in said solvent is 10.

Said compound of formula (I) can be a solid, semisolid, waxy or oil form.

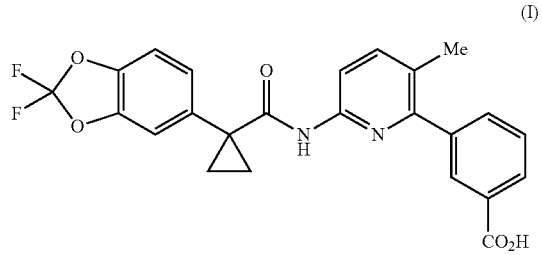 [SMILES: Cc1ccc(NC(=O)C2(c3ccc4c(c3)OC(F)(F)O4)CC2)nc1-c1cccc(C(=O)O)c1]

(I)

Another objective of the disclosure is to provide a pharmaceutical composition comprising a therapeutically effective amount of crystalline Form A of compound of formula (I) and pharmaceutically acceptable excipient. Generally, a therapeutically effective amount of crystalline Form A of compound of formula (I) is mixed or contacted with one or more pharmaceutical acceptable excipients to make pharmaceutical composition or formulation, and the pharmaceutical composition or formulation are prepared by well-known method in the pharmaceutical field.

Another objective of the disclosure is to provide a pharmaceutical composition comprising a therapeutically effective amount of crystalline Form A of compound of formula (I), Ivacaftor and pharmaceutically acceptable excipient. Generally, a therapeutically effective amount of crystalline Form A of compound of formula (I) and Ivacaftor are mixed or contacted with one or more pharmaceutical excipients to make pharmaceutical composition or formulation, and the pharmaceutical composition or formulation are prepared by well-known method in the pharmaceutical field.

The pharmaceutical composition above can be developed into a certain dosage form, and is administrated by a suitable route. Dosage form such as: solid oral dosage forms, including but not limited to powders, granules, pills, tablets and capsules; Liquid oral dosage forms, including but not limited to sirups, suspensions, dispersants and emulsions; and injections, including but not limited to solutions, dispersants and lyophilized formulations. Dosage forms may be instant-release, delayed-release or time controlled-release and instant-release may be common, dispersal, chewable, orally disintegrating or instant. Time controlled-release may be a skeleton or repository system that consists of hydrophilic, hydrophobic material or a combination of hydrophilic and hydrophobic material to control the release rate. The formulation process is possible to use the method such as direct compression, dry granulation, wet granulation and extrusion-spheronization. The possible presentation of the dosage form includes un-coating, film coating, sugar coating, powder coating, enteric coating or sustained-release coating. The administration route such as oral administration and parenteral administration (including subcutaneous, muscle, vein or skin), rectal, transdermal, nasal and vagina, and so on. The dosage form suitable for oral administration comprises tablets, capsules, granules, powders and pills, a powder, an ingot, a solution, a syrup or a suspension according to needs, and can be used for rapid release, delayed release or regulation release of active pharmaceutical ingredients. The dosage form suitable for parenteral administration comprises an aqueous or non-aqueous sterile injection solution, an emulsion or a suspension. The dosage form suitable for rectal administration comprises a suppository or an enema. The dosage form suitable for transdermal administration comprises an ointment, a cream and a patch. The dosage form suitable for nasal administration comprises an aerosol, a spray and a nose drop. The dosage form suitable for vaginal administration comprises a suppository, a plugging agent and a gel, a paste or a spray.

Furthermore, crystalline Form A of compound of formula (I) or the pharmaceutical composition thereof can be used for preparing drugs for treating cystic fibrosis.

Furthermore, crystalline Form A of compound of formula (I) or the pharmaceutical composition thereof can be used in combination with one or more drugs for preparing drugs for treating cystic fibrosis.

Furthermore, crystalline Form A of compound of formula (I) or the pharmaceutical composition thereof can be used in combination with Ivacaftor for preparing drugs for treating cystic fibrosis.

The present disclosure relates to methods of treating patients with CFTR mediated disease and the method comprising administrating an effective amount of crystalline Form A of compound of formula (I) or the pharmaceutical composition thereof. Preferably, the present disclosure relates to methods of treating patients with cystic fibrosis and the method comprising administrating an effective amount of crystalline Form A of compound of formula (I) or the pharmaceutical composition thereof.

The present disclosure relates to methods of treating patients with CFTR mediated disease and the methods comprising administrating an effective amount of combination of crystalline Form A of compound of formula (I) and Ivacaftor. Preferably, the present disclosure also relates to methods of treating patients with cystic fibrosis and the method comprising administrating an effective amount of combination of crystalline Form A of compound of formula (I) and Ivacaftor.

The said CFTR mediated disease is selected from cystic fibrosis, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulinemia, diabetes mellitus, Laron dwarfism, myeloperoxidase deficiency, primary hyperparathyroidism, melanoma, glycan CDG type 1, hereditary emphysema, congenital hyperthyroidism, osteogenesis imperfecta, hereditary hypofibrinogenemia, ACT deficiency, diabetes insipidus (DI), neurophyseal of DI, nephrogenic DI, Charcot-Marie Tooth syndrome, Pelizaeus-Merzbacher disease, neurodegenerative diseases such as Alzheimer's disease, amyotrophic lateral sclerosis, progressive supranuclear palsy, Pick's disease, several polyglutamine neurological disorders such as Huntington, Spinocerebellar ataxia type I, spinal and bulbar muscular atrophy, dentatorubal pallidoluysian, and myotonic dystrophy, as well as spongiform encephalopathies, Parkinson's disease.

The terms in the present disclosure have common sense to those skilled in the art if there is no definition.

The term "effective treatment amount" or "therapeutically effective amount" as used herein means that amount of an active compound that elicits the biological or medicinal response in a tissue, system, animal or human that is being sought by a researcher, veterinarian, medical doctor, or other clinician.

As used herein, the term "treatment" refers to one or more of the following: (1) Preventing disease, for example, preventing the disease, illness or disorder in an individual who may be suffering from a disease, illness or disorder but not suffering from or displaying a lesion or symptom of the disease, (2) Inhibiting the disease, for example, inhibiting the disease, illness or disorder in an individual who is suffering from or displaying a lesion or symptom of the disease, illness or disorder, and (3) Improving the disease, for example, improving the disease, illness or disorder in an individual who is suffering from or displaying a lesion or symptom of the disease, illness or disorder (that is to reverse the lesion and/or symptoms), for example, reducing the severity of the disease.

As used herein, the term "polymorphic form" refers to different crystalline forms of the same compound and includes, but is not limited to other solid forms including hydrates and solvates of the same compound. The phenomenon that the same drug molecule forms a variety of crystalline forms is called drug polymorphism, drug polymorphism is a phenomenon commonly found in solid drugs. It is known that pharmaceutical compounds having such polymorphs have an influence on pharmacological activity, solubility, bioavailability and stability due to their different physical and chemical properties. Therefore, in the case where a compound useful as a drug has polymorphic forms, it is desirable to produce a crystalline compound that is more useful from these polymorphs.

The term "X-ray powder diffraction pattern" as used herein refers to a diffraction pattern observed by an experiment or a parameter derived therefrom. The X-ray powder diffraction pattern is characterized by the peak position and the peak intensity.

The present disclosure has the following advantages:

The novel crystalline form of compound of formula (I) in present disclosure has higher solubility than Form I in prior art, it is of great value in improving drug efficacy and reducing drug-loading. In addition, the crystalline Form A has good stability and it is easy to be prepared directly from the free form of compound, which is suitable for the development of the drug.

DETAILED DESCRIPTION OF THE DISCLOSURE

The present disclosure will be further explained by the specific embodiments, but are not intended to limit the scope of the present disclosure. In the following examples, general conditions or conditions recommended by the manufacturer are used in tests methods; the said compound of Lumacaftor was obtained commercially.

The experimental conditions not specified are general conditions.

The abbreviations used in the disclosure are explained as follows:

XRPD: X-ray Powder Diffraction
DSC: Differential Scanning calorimetry
$^1$H NMR: $^1$H Nuclear Magnetic Resonance
DVS: Dynamic Vapor Sorption
PLM: Polarized Light Microscopy
IR: Infrared Radiation X-ray powder diffraction pattern in the present disclosure was acquired by a Panalytical Empyrean X-ray powder diffractometer. The parameters of the X-ray powder diffraction method of the present disclosure were as follows:

X-ray Reflection: Cu, Kα
Kα1 (Å): 1.540598; Kα2 (A): 1.544426
Kα2/Kα1 intensity ratio: 0.50
Voltage: 45 (kV)
Current: 40 (mA)
Scan range: from 3.0 degree to 40.0 degree Differential scanning calorimetry (DSC) data in the present disclosure were acquired by a TA Q2000. The parameters of the differential scanning calorimetry (DSC) method of the present disclosure were as follows:

Heating rate: 10° C./min
Purge gas: nitrogen

Dynamic vapor sorption (DVS) data in the present disclosure was acquired by a SMS (Surface Measurement Systems Ltd.) DVS Intrinsic. About 10 mg of crystalline Form A of present disclosure was used for DVS test. The parameters of the dynamic vapor sorption (DVS) method of the present disclosure were as follows:

Temperature: 25° C.
Gas and flow rate: $N_2$, 200 mL/min
dm/dt: 0.002%/min
RH range: 0% RH to 95% RH
Stable duration: 10 min
Maximum equilibrate time: 180 min
Humidity gradient: 10% (0% RH-90% RH), 5% (90% RH-95% RH).

Polarized light microscope (PLM) image in the present disclosure were acquired by a ZEISS Axio Lab.A1 upright microscope.

Infrared radiation (IR) spectrum in the present disclosure was acquired by a Nicolet 6700 Fourier Transform Infrared Spectrometer (Thermo Fisher Scientific). The parameters of the Fourier Transform Infrared Spectrometer method of the present disclosure were as follows:
Light: infrared light
Detector: DTGS
Beam splitter: KBr
Number of scans: 32
Resolution: 4.000

Example 1

Process for Preparing Crystalline Form A of the Compound of Formula (I):

5.3 mg of the compound of formula (I) was dissolved into 0.5 mL methyl isobutyl ketone. Then the solution was evaporated at 50° C. for three days. The obtained white solid was identified as crystalline Form A.

Figure 1:
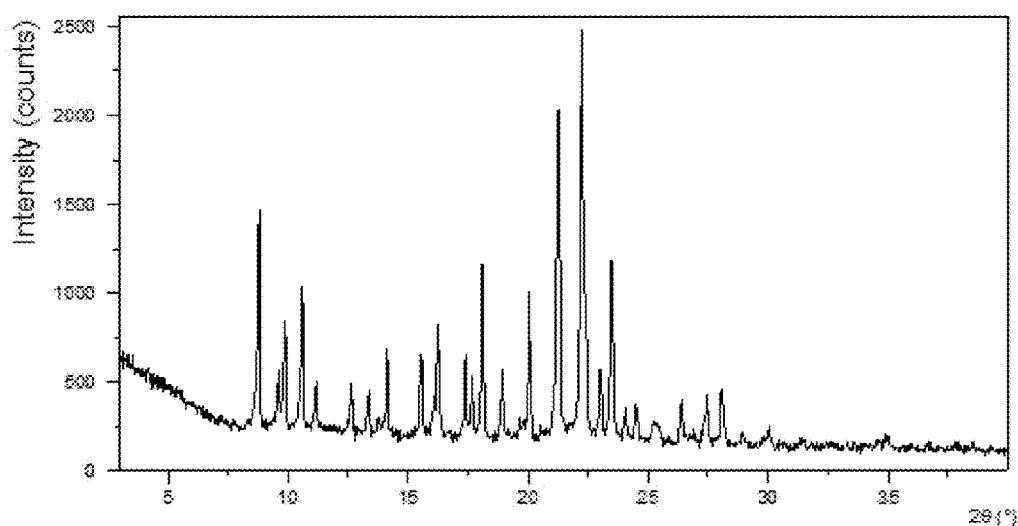
FIG. 1 shows an XRPD pattern of crystalline Form A.

The XRPD data of crystalline Form A prepared in this example are including but not limited to the data listed in Table 1. The XRPD pattern is displayed in FIG. 1.

TABLE 1

The XRPD data of crystalline Form A

| 2theta | d spacing | Intensity % |
|---|---|---|
| 8.77 | 10.08 | 52.78 |
| 9.58 | 9.24 | 13.30 |
| 9.85 | 8.98 | 24.45 |
| 10.56 | 8.38 | 35.38 |
| 11.14 | 7.94 | 11.76 |
| 12.60 | 7.02 | 11.70 |
| 13.35 | 6.63 | 10.08 |
| 14.13 | 6.27 | 20.29 |
| 15.54 | 5.70 | 19.57 |
| 16.23 | 5.46 | 28.07 |
| 17.38 | 5.10 | 20.11 |
| 17.65 | 5.03 | 14.66 |
| 18.10 | 4.90 | 40.65 |
| 18.92 | 4.69 | 16.40 |
| 20.04 | 4.43 | 32.37 |
| 21.25 | 4.18 | 83.17 |
| 22.21 | 4.00 | 100.00 |
| 23.00 | 3.87 | 18.04 |
| 23.46 | 3.79 | 43.79 |
| 24.03 | 3.70 | 8.68 |
| 24.50 | 3.63 | 7.46 |
| 25.42 | 3.50 | 4.38 |
| 26.39 | 3.38 | 9.83 |
| 27.45 | 3.25 | 10.73 |
| 28.05 | 3.18 | 14.01 |
| 28.95 | 3.08 | 1.96 |
| 30.02 | 2.98 | 3.95 |
| 34.98 | 2.57 | 2.12 |

Figure 2:
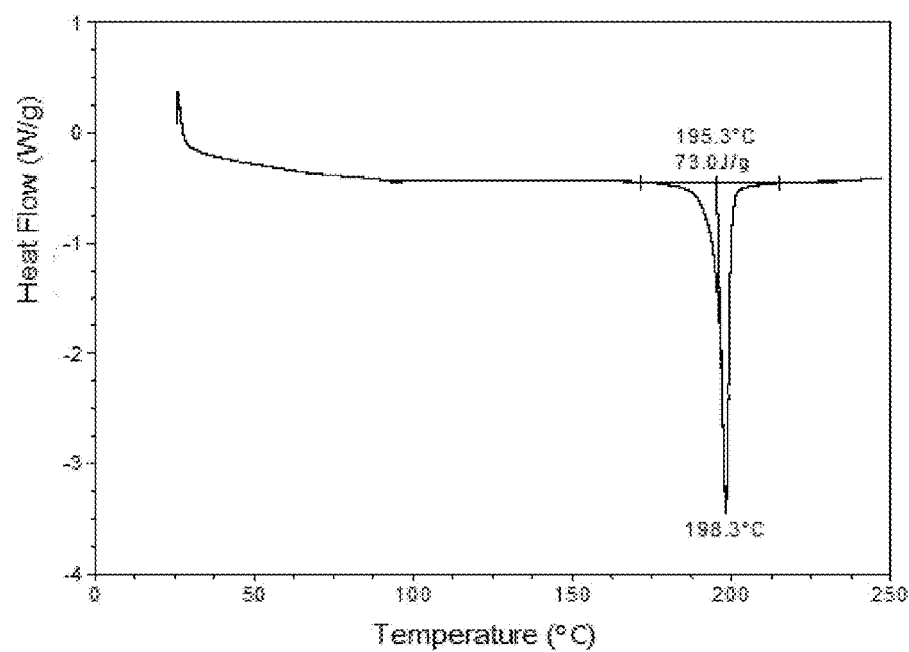
FIG. 2 shows a DSC thermogram of crystalline Form A.

The DSC thermogram of crystalline Form A shows an endothermic peak when heated to around 195° C. (onset temperature), which is substantially depicted in FIG. 2.

Figure 3:
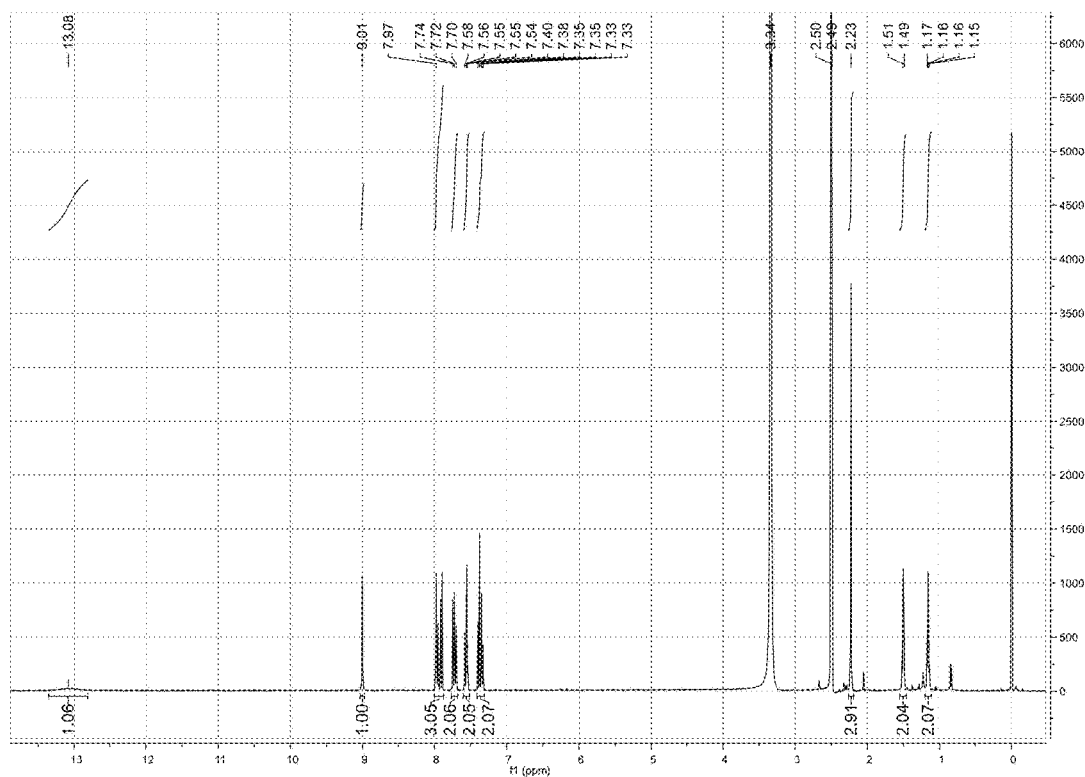
FIG. 3 shows a $^1$H NMR spectrum of crystalline Form A.
Figure 4:
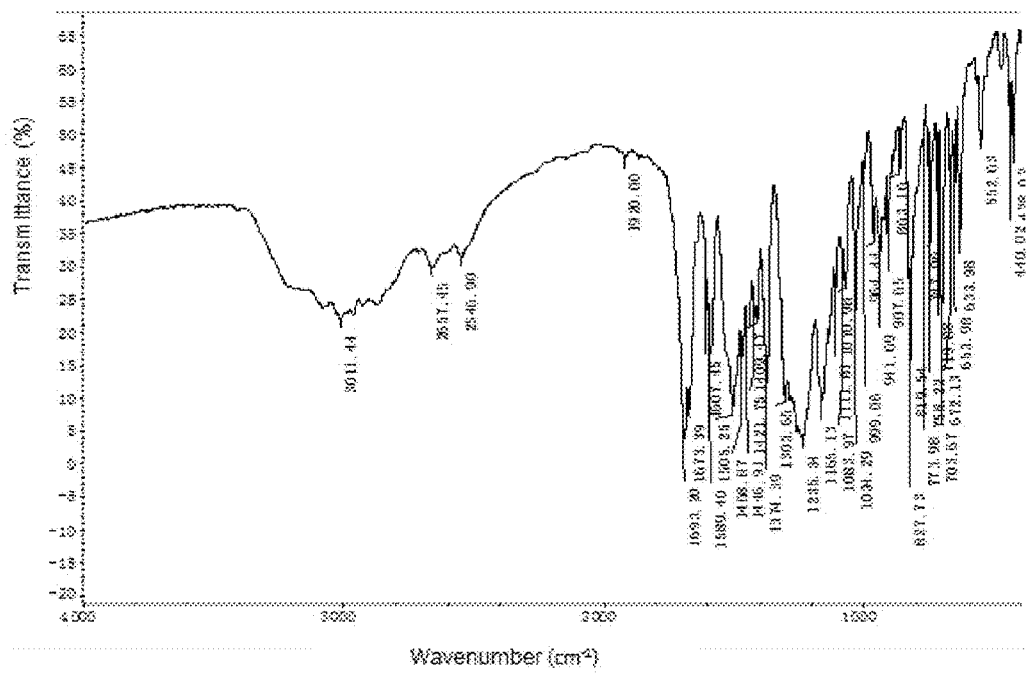
FIG. 4 shows an IR spectrum of crystalline Form A.

The $^1$H NMR spectrum of crystalline Form A is displayed in FIG. 3. The $^1$H NMR data are as follows:

$^1$H NMR (400 MHz, DMSO) δ 13.08 (s, 1H), 9.01 (s, 1H), 8.00-7.87 (m, 3H), 7.77-7.68 (m, 2H), 7.60-7.51 (m, 2H), 7.35 (dt, J=8.3, 5.0 Hz, 2H), 2.23 (s, 3H), 1.51 (q, J=4.1 Hz, 2H), 1.16 (dd, J=7.0, 4.2 Hz, 2H)

Example 2

Process for Preparing Crystalline Form A of the Compound of Formula (I):

5.4 mg of the compound of formula (I) was dissolved into 0.5 mL mixture of acetone and methyl tertiary butyl ether (The volume ratio of acetone and methyl tertiary butyl ether is 1:2.). Then the solution was evaporated at 50° C. for three days. The obtained white solid was identified as crystalline Form A.

The XRPD data of crystalline Form A prepared in this example are including but not limited to the data listed in Table 2.

TABLE 2

The XRPD data of crystalline Form A

| 2theta | d spacing | Intensity % |
|---|---|---|
| 8.77 | 10.08 | 55.12 |
| 9.86 | 8.97 | 17.80 |
| 10.56 | 8.38 | 35.17 |
| 11.13 | 7.95 | 4.50 |
| 12.61 | 7.02 | 6.16 |
| 14.14 | 6.27 | 29.04 |
| 15.54 | 5.70 | 13.39 |
| 16.24 | 5.46 | 26.21 |
| 17.38 | 5.10 | 10.27 |
| 17.66 | 5.02 | 9.46 |
| 18.10 | 4.90 | 35.72 |
| 18.91 | 4.69 | 10.83 |
| 20.05 | 4.43 | 24.97 |
| 21.26 | 4.18 | 100.00 |
| 22.21 | 4.00 | 90.23 |
| 22.99 | 3.87 | 17.07 |
| 23.46 | 3.79 | 31.12 |
| 24.05 | 3.70 | 6.80 |
| 24.49 | 3.63 | 9.87 |
| 25.30 | 3.52 | 2.62 |
| 26.39 | 3.38 | 8.06 |
| 27.43 | 3.25 | 7.17 |
| 28.07 | 3.18 | 11.73 |

Example 3

Process for Preparing Crystalline Form a of the Compound of Formula (I):

10.1 mg of the compound of formula (I) was dissolved into 1.0 mL of methyl isobutyl ketone. Then the solution was evaporated at 50° C. for three days. The obtained white solid was identified as crystalline Form A.

The XRPD data of crystalline Form A prepared in this example are including but not limited to the data listed in Table 3.

TABLE 3

The XRPD data of crystalline Form A

| 2theta | d spacing | Intensity % |
|---|---|---|
| 8.77 | 10.08 | 70.87 |
| 9.85 | 8.98 | 11.77 |
| 10.56 | 8.38 | 50.38 |
| 11.15 | 7.94 | 5.84 |
| 12.62 | 7.02 | 6.50 |
| 13.36 | 6.63 | 15.57 |
| 14.14 | 6.27 | 24.94 |
| 15.54 | 5.70 | 14.46 |
| 16.24 | 5.46 | 47.68 |
| 16.76 | 5.29 | 3.05 |
| 17.38 | 5.10 | 6.13 |
| 17.65 | 5.02 | 11.64 |
| 18.10 | 4.90 | 27.67 |
| 18.91 | 4.69 | 11.92 |
| 20.05 | 4.43 | 41.72 |
| 21.26 | 4.18 | 100.00 |
| 22.21 | 4.00 | 79.65 |
| 23.01 | 3.87 | 23.02 |
| 23.47 | 3.79 | 37.10 |
| 24.03 | 3.70 | 6.64 |
| 24.49 | 3.63 | 7.32 |
| 25.30 | 3.52 | 2.01 |
| 26.42 | 3.37 | 4.81 |
| 27.46 | 3.25 | 13.07 |

TABLE 3-continued

| The XRPD data of crystalline Form A | | |
|---|---|---|
| 2theta | d spacing | Intensity % |
| 28.06 | 3.18 | 24.23 |
| 34.94 | 2.57 | 1.39 |

Example 4

Figure 5:
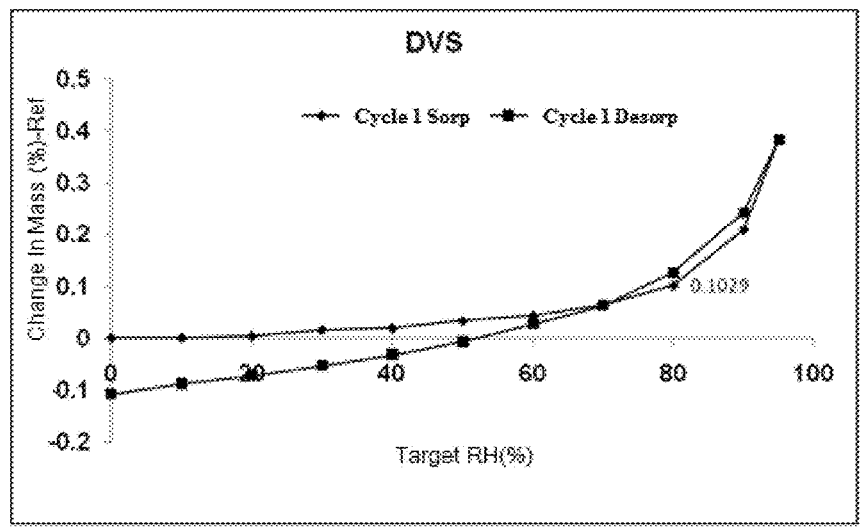
FIG. 5 shows a DVS plot of crystalline Form A.
Figure 6:
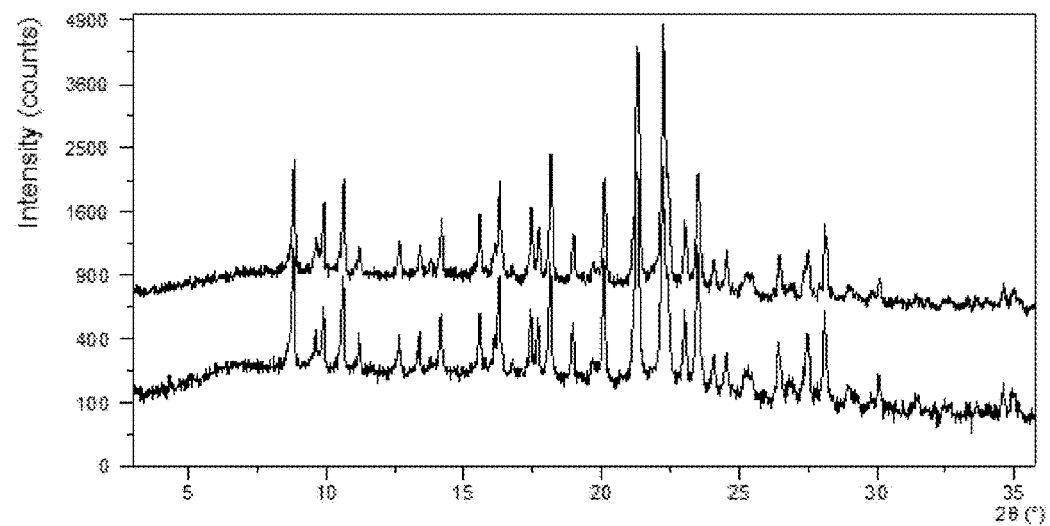
FIG. 6 shows an XRPD comparison pattern of crystalline Form A before and after DVS (the pattern above is before DVS and the below one is after DVS).

Hygroscopicity Assessment of Crystalline Form A of Compound of Formula (I):

About 12.2 mg of crystalline Form A of the present disclosure was used for hygroscopicity testing using dynamic vapor sorption (DVS), crystalline Form A underwent a 0-95%-0 cycle of the relative humidity (RH) change. The result is listed in Table. 4. The DVS isotherm plot of crystalline Form A is shown in FIG. 5. The XRPD patterns of crystalline Form A before and after hygroscopicity assessment are depicted in FIG. 6. The pattern above is before DVS and the below one is after DVS. This result shown that crystalline Form A didn't change after DVS test.

TABLE 4

| Solid Form | Weight Gain under 80% Relative Humidity |
|---|---|
| Crystalline Form A of the compound of formula (I) | 0.10% |

About hygroscopicity characterization description and definition of hygroscopicity (Chinese Pharmacopoeia 2010 edition appendix XIV Drug hygroscopic test guidelines, test at 25° C.+/−1° C., 80% Relative Humidity)
  deliquescent: sufficient water is absorbed to form a liquid.
  very hygroscopic: increase in mass is equal to or greater than 15%.
  hygroscopic: increase in mass is less than 15% and equal to or greater than 2%.
  slightly hygroscopic: increase in mass is less than 2% and equal to or greater than 0.2%.
  no or almost no hygroscopic: increase in mass is less than 0.2%.

The result shows that weight gain of crystalline Form A of the compound of formula (I) of the present disclosure is 0.10% at 80% RH. According to the criteria of hygroscopicity, Form A is a non-hygroscopic or almost non-hygroscopic form. This property indicates that the crystalline Form A is not sensitive to moisture and it is convenient for long-term storage. On the other hand, no special drying conditions are required in the preparation process due to its low hygroscopicity, which simplifies the preparation and post-treatment process to some extent, and the process is easy to be industrialized.

Example 5

Figure 7:
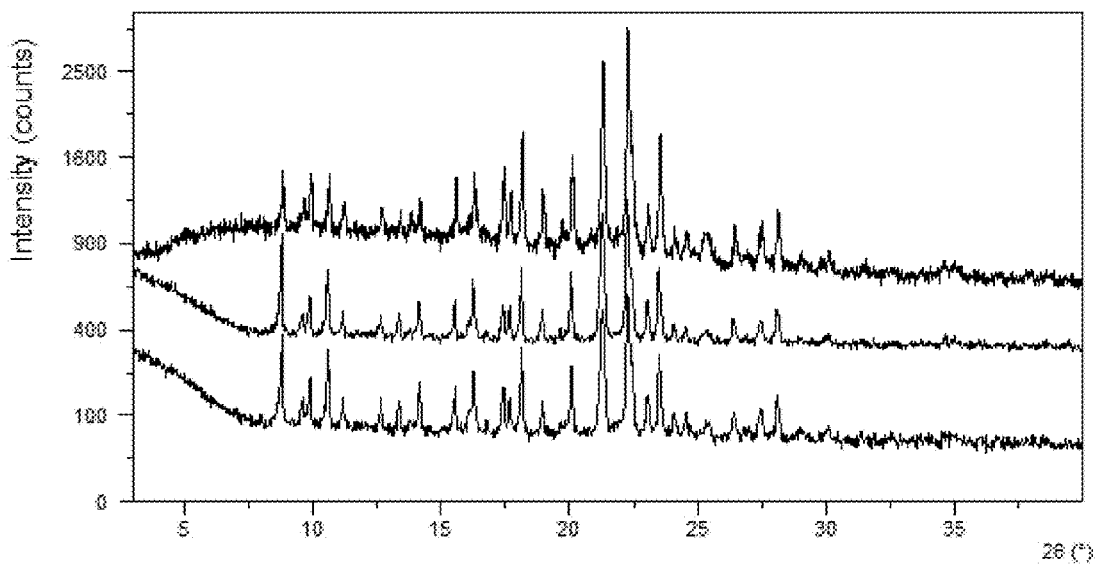
FIG. 7 shows an XRPD overlay pattern of crystalline Form A after storing at 25° C./60% RH and 40° C./75% RH for 90 days (the top, middle and bottom patterns are initial crystalline Form A, crystalline Form A after storing at 25° C./60% RH and 40° C./75% RH for 90 days, respectively).

Stability Assessment of Crystalline Form a of the Compound of Formula (I):

The crystalline Form A of the compound of formula (I) of the present disclosure was stored under 25° C./60% RH and 40° C./75% RH for 90 days. XRPD and purity of the samples were collected after storing for 15 days, 30 days and 90 days. The results indicate that crystalline Form A has good physical stability and high chemical purity. The chemical purity data are shown in Table 5. The XRPD results of crystalline Form A before and after storing under 25° C./60% RH and 40° C./75% RH for 90 days are depicted in FIG. 7 (FIG. 7: the top, middle and bottom are initial crystalline Form A, crystalline Form A after storing at 25° C./60% RH and 40° C./75% RH for 90 days respectively).

TABLE 5

| Stability of crystalline Form A (Purity %) | | |
|---|---|---|
|  | 25° C./60% RH/% | 40° C./75% RH/% |
| Initial | 99.82 | 99.82 |
| 15 days | 99.94 | 99.94 |
| 30 days | 99.90 | 99.94 |
| 90 days | 99.93 | 99.94 |

The results show that the crystalline Form A of the compound of formula (I) is stable under long-term stability condition (25° C./60% RH) and accelerated stability condition (40° C./75% RH), and the chemical purity is almost unchanged. Therefore, the crystalline Form A of the compound of formula (I) of the present disclosure has good physical stability and high chemical purity.

Example 6

Solubility Comparison of Crystalline Form A of the Compound Formula (I) and Form I Disclosed in CN101910156A:

Crystalline Form A of the present disclosure and Form I disclosed in CN101910156A are prepared into saturated solution in SGF (Simulated gastric fluids), pH5.0 FeSSIF (Fed state simulated intestinal fluids), pH6.5 FaSSIF (Fasted state simulated intestinal fluids) and water. Concentrations in the saturation solutions were tested after 1 hour, 4 hours and 24 hours by HPLC. The results are listed in Table 6.

TABLE 6

| Solubility comparison of crystalline Form A and Form I disclosed in CN101910156A | | | | | | | | |
|---|---|---|---|---|---|---|---|---|
|  | Solubility | | | | | | | |
|  | SGF | | FaSSIF | | FeSSIF | | $H_2O$ | |
| Sampling Time | Form A (mg/mL) | Form I (mg/mL) | Form A (mg/mL) | Form I (mg/mL) | Form A (mg/mL) | Form I (mg/mL) | Form A (mg/mL) | Form I (mg/mL) |
| 1 hour | 0.0009 | 0.0004 | 0.0082 | 0.0023 | 0.017 | 0.0055 | 0.0086 | 0.0022 |
| 4 hours | 0.0019 | <0.00022 | 0.011 | 0.0015 | 0.018 | 0.0059 | 0.016 | 0.0067 |
| 24 hours | 0.002 | <0.00021 | 0.0095 | 0.0009 | 0.02 | 0.0055 | 0.025 | 0.016 |

The comparison results above indicate that the solubility of crystalline Form A of the present disclosure is higher than that of Form I disclosed in CN101910156A in SGF, FaSSIF, FeSSIF and H₂O after 1 hour, 2 hours and 24 hours. Therefore, crystalline Form A of the present disclosure can improve drug's bioavailability, and is more suitable for drug development.

Example 7

Figure 8:
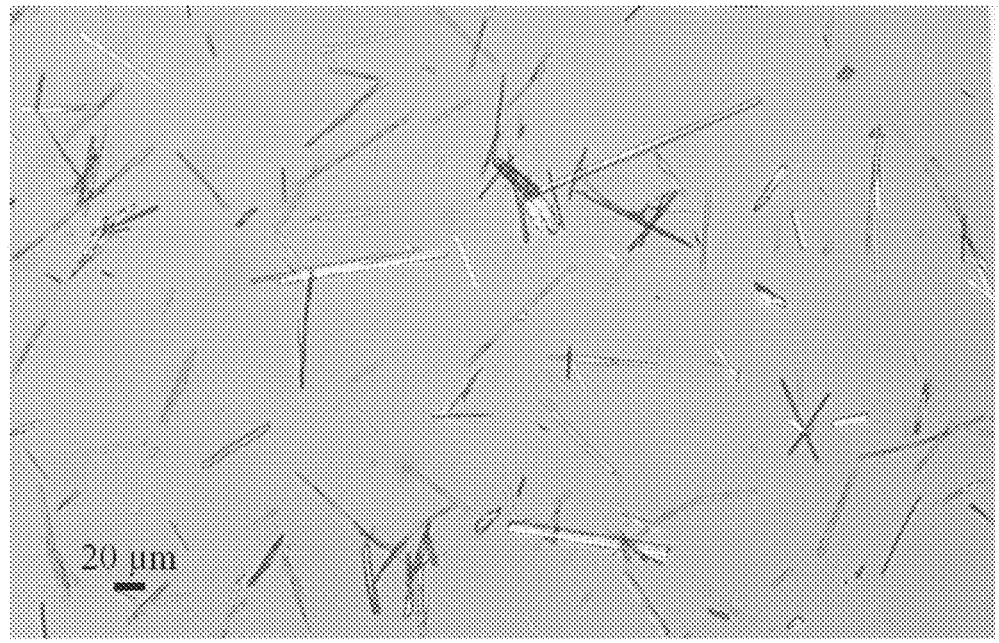
FIG. 8 shows a PLM image of crystalline Form I.
Figure 9:
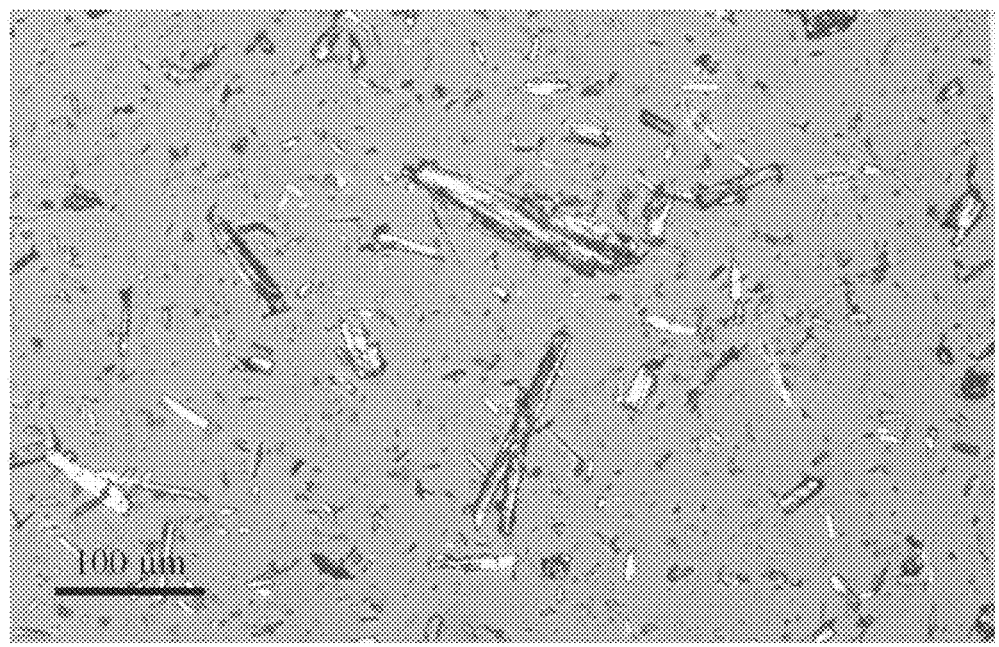
FIG. 9 shows a PLM image of crystalline Form A.

Method of PLM test: placed about 0.5 mg of the sample on a glass slide and add a small amount of mineral oil to disperse the sample. After covering the coverslip, gently press with fingertips to ensure that there is no bubble between the glass slide and coverslip. Then adjust the eyepiece and objective lenses of the microscope and fine-tune the sample stage to focus on the sample. The PLM results of Form I disclosed in CN101910156A and Form A of the present disclosure are shown in FIG. 8 and FIG. 9, respectively. Form I disclosed in CN101910156A has a needle-like shape, while Form A of the present disclosure has a long rod-like shape. Therefore, Form A of the present disclosure has better fluidity, and is more suitable for process development.

It should be noted that the reason why the compound of formula (I) in solid state is used as the starting material in the above examples is that the compound of formula (I) in solid state is easier to obtain, and it does not mean that only solid state form can be used. The said compound of formula (I) can be in solid, semi-solid, waxy or oil forms. According to the inventors' experiments, the final crystalline form is closely related to the preparation conditions and methods, regardless of the physical state of the starting material.

The examples described above are only for illustrating the technical concepts and features of the present disclosure, and intended to make those skilled in the art being able to understand the present disclosure and thereby implement it, and should not be concluded to limit the protective scope of this disclosure. Any equivalent variations or modifications according to the spirit of the present disclosure should be covered by the protective scope of the present disclosure.

The invention claimed is:
1. A crystalline Form A of compound of formula (I),

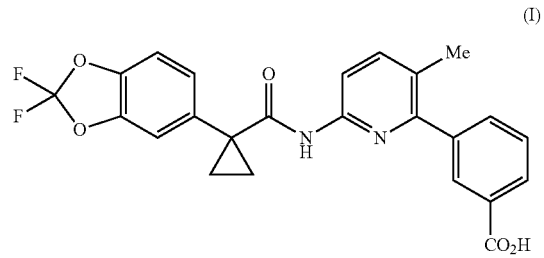 [SMILES: Cc1ccc(NC(=O)C2(c3ccc4c(c3)OC(F)(F)O4)CC2)nc1-c1cccc(C(=O)O)c1]

wherein the X-ray powder diffraction pattern shows characteristic peaks at 2theta values of 8.8°±0.2°, 9.8°±0.2°, 10.6°±0.2°, 16.2°±0.2°, 18.1°±0.2°, 20.0°±0.2°, 21.2°±0.2°, 22.2°±0.2° 23.5°±0.2°.

2. A process of preparing crystalline Form A of compound of formula (I) according to claim 1, comprising dissolving compound of formula (I) in methyl isobutyl ketone or the mixture of acetone or methyl isobutyl ketone and methyl tertiary butyl ether, and obtaining a white solid by evaporation at the temperature of 20° C.-80° C., wherein the volume ratio of acetone or methyl isobutyl ketone and methyl tertiary butyl ether is 1:1 to 1:4.

3. The process according to claim 2, wherein said temperature is 30° C.~70° C.

4. The process according to claim 3, wherein said temperature is 40° C.~60° C.

5. A pharmaceutical composition, wherein the said pharmaceutical composition comprises a therapeutically effective amount of crystalline Form A according to claim 1 and pharmaceutically acceptable excipient.

6. A method of treating cystic fibrosis in a subject thereof, comprising administering the crystalline Form A according to claim 1 to the subject.

7. A method of treating cystic fibrosis in a subject thereof, comprising administering the crystalline Form A according to claim 1 to the subject in combination with one or more drugs.

8. A method of treating cystic fibrosis in a subject thereof, comprising administering the crystalline Form A according to claim 1 to the subject in combination with Ivacaftor.

* * * * *